United States Patent
Suhr (10) Patent No.: US 10,821,271 B2
(45) Date of Patent: Nov. 3, 2020

(54) SIDE BRANCH ACCESSIBLE BALLOON FOR BIFURCATION STENTING

(76) Inventor: William S. Suhr, South Barrington, IL (US)

(\*) Notice: Subject to any disclaimer, the term of this patent is extended or adjusted under 35 U.S.C. 154(b) by 0 days.

(21) Appl. No.: 13/579,696

(22) PCT Filed: Feb. 18, 2011

(86) PCT No.: PCT/US2011/000321
§ 371 (c)(1),
(2), (4) Date: Nov. 2, 2012

(87) PCT Pub. No.: WO2011/109067
PCT Pub. Date: Sep. 9, 2011

(65) Prior Publication Data
US 2013/0053940 A1  Feb. 28, 2013

Related U.S. Application Data

(60) Provisional application No. 61/340,814, filed on Mar. 22, 2010, provisional application No. 61/338,528, filed on Feb. 18, 2010.

(51) Int. Cl.
*A61F 2/954* (2013.01)
*A61F 2/958* (2013.01)
(Continued)

(52) U.S. Cl.
CPC ......... *A61M 25/1011* (2013.01); *A61F 2/954* (2013.01); *A61F 2/958* (2013.01);
(Continued)

(58) Field of Classification Search
CPC .......... A61F 2/852; A61F 2/856; A61F 2/954; A61F 2/958; A61F 2002/9505;
(Continued)

(56) References Cited

U.S. PATENT DOCUMENTS

| 4,877,031 A | \* | 10/1989 | Conway et al. ............... 606/194 |
| 5,795,331 A | \* | 8/1998 | Cragg .............. A61B 17/12022 |
| | | | 604/103.01 |
| 6,494,905 B1 | \* | 12/2002 | Zedler et al. ................. 623/1.11 |
| 6,527,790 B2 | \* | 3/2003 | Chien et al. ................... 606/194 |

(Continued)

OTHER PUBLICATIONS

Screen shot of Vention Medical, Inc. on-line catalog for "Medical Balloon Item No. 08004017FA", URL: http://www.ventionmedical.com/products-and-services/advanced-polymers/medical-balloons/catalog/ItemDetails.aspx?ItemNumber=08004017FA (original publication date unknown).

*Primary Examiner* — Darwin P Erezo
*Assistant Examiner* — Christian D. Knauss
(74) *Attorney, Agent, or Firm* — Henry C. Query, Jr.

(57) ABSTRACT

A balloon catheter for treating a condition of a vessel near a bifurcation comprises a shaft including a proximal and distal end, and a side surface, at least one guide wire lumen extending longitudinally, a distal port extending from the guide wire lumen through the distal end, a side port extending transversely from the guide wire lumen through the side surface, and a balloon mounted on the shaft. The balloon comprises a first end sealed to the shaft proximally of the side port, a second end sealed to the shaft distally of the side port and an aperture aligned with the side port. A portion of the balloon surrounding the aperture is sealed to the shaft around the side port. The balloon may be guided to the bifurcation on a first and a second guide wires pre-positioned in main and in side branch vessel, respectively.

8 Claims, 6 Drawing Sheets (51) Int. Cl.
*A61M 25/10* (2013.01)
*A61M 25/00* (2006.01)
*A61F 2/856* (2013.01)
*A61F 2/852* (2013.01)

(52) U.S. Cl.
CPC ............... *A61F 2/852* (2013.01); *A61F 2/856* (2013.01); *A61F 2250/006* (2013.01); *A61M 25/0029* (2013.01); *A61M 25/0032* (2013.01); *A61M 2025/1045* (2013.01)

(58) Field of Classification Search
CPC .... A61F 2002/9522; A61F 2002/9583; A61M 25/0029; A61M 25/1011; A61M 2025/1045; A61M 25/0032; A61M 25/10; A61M 25/1002; A61M 25/1027; A61M 25/1034
USPC .................... 623/1.11, 1.13, 1.16, 1.23, 1.35
See application file for complete search history.

(56) References Cited

U.S. PATENT DOCUMENTS

| | | | |
|---|---|---|---|
| 6,579,309 B1* | 6/2003 | Loos et al. | 623/1.16 |
| 6,582,394 B1* | 6/2003 | Reiss et al. | 604/96.01 |
| 6,761,734 B2* | 7/2004 | Suhr | 623/1.35 |
| 7,323,009 B2* | 1/2008 | Suhr et al. | 623/1.35 |
| 7,871,431 B2* | 1/2011 | Gurm et al. | 623/1.11 |
| 8,012,199 B2* | 9/2011 | Lualdi | 623/1.35 |
| 2001/0037138 A1* | 11/2001 | Wilson et al. | 623/1.11 |
| 2002/0035392 A1* | 3/2002 | Wilson | 623/1.11 |
| 2003/0187494 A1* | 10/2003 | Loaldi | A61F 2/856 623/1.11 |
| 2004/0015231 A1* | 1/2004 | Suhr | A61F 2/954 623/1.35 |
| 2004/0138732 A1* | 7/2004 | Suhr et al. | 623/1.11 |
| 2005/0060027 A1* | 3/2005 | Khenansho et al. | 623/1.35 |
| 2005/0222666 A1* | 10/2005 | Lualdi | 623/1.12 |
| 2007/0016241 A1 | 1/2007 | von Oepen et al. | |
| 2007/0260217 A1* | 11/2007 | Von Oepen et al. | 604/509 |
| 2008/0086191 A1* | 4/2008 | Valencia et al. | 623/1.11 |
| 2009/0299457 A1* | 12/2009 | Lualdi | 623/1.11 |

* cited by examiner

SIDE BRANCH ACCESSIBLE BALLOON FOR BIFURCATION STENTING

This application is based on and claims priority from U.S. Provisional Patent Application No. 61/338,528 filed on Feb. 18, 2010 and U.S. Provisional Patent Application No. 61/340,814 filed on Mar. 22, 2010.

BACKGROUND OF THE INVENTION

The present invention relates to a balloon catheter which may be used to deploy one or more stents in a bifurcation of a blood vessel in order to treat an occlusion or lesion occurring in or near the bifurcation.

Balloon catheters are commonly used to treat certain conditions of a blood vessel, such as a partial or total occlusion or lesion of the vessel which may be caused by, for example, atherosclerotic plagues or thrombosis. In an angioplasty procedure, the balloon portion of the catheter is advanced over a guide wire to the site of the occlusion and inflated to compress the occlusion and thereby restore normal blood flow through the vessel. In some instances, a stent may be implanted in the blood vessel to prevent the occlusion from recurring. A balloon catheter is commonly used to deliver and deploy the stent in such a stenting or stent implantation procedure. The stent is typically mounted on the balloon portion of the catheter, delivered to the site of the occlusion and then deployed or implanted in the vessel by inflating the balloon portion.

Prior art stenting procedures often are unsuitable for treating a condition of a blood vessel occurring at or near a bifurcation of the blood vessel, that is, the intersection of a main vessel with a side branch vessel. One method for stenting an occlusion in a bifurcation involves implanting a first stent in the main vessel adjacent the bifurcation and then implanting a second stent in the side branch vessel adjacent the bifurcation (the so-called "T-stenting" procedure). However, this requires that the guide wire for the balloon catheter which is used to deliver the second stent be threaded through the struts of the first stent and into the side branch vessel. This process can be quite difficult and time consuming. Furthermore, the stenting of the main vessel may shift plagues and thereby close off the side branch vessel, making it extremely difficult to insert the guide wire into the side branch vessel.

SUMMARY OF THE INVENTION

These and other limitations in the prior art are addressed by providing a novel balloon catheter for use in treating a condition of a vessel occurring near a bifurcation. The balloon catheter comprises a shaft which includes a proximal end, a distal end and a side surface; at least one guide wire lumen which extends longitudinally through the shaft; a distal port which extends from the guide wire lumen through the distal end of the shaft; a side port which extends transversely from the guide wire lumen through the side surface of the shaft; and a balloon which is mounted on the shaft. The balloon comprises a first end which is sealed to the shaft proximally of the side port, a second end which is sealed to the shaft distally of the side port and an aperture which is aligned with the side port. In addition, a portion of the balloon surrounding the aperture is sealed to the shaft around the side port.

In use, a proximal end of a first guide wire which is pre-positioned in the main vessel may be inserted into the distal port and threaded through the guide wire lumen toward the proximal end of the shaft. Also, a proximal end of a second guide wire which is pre-positioned in the side branch vessel may be inserted into the side port and threaded through the guide wire lumen toward the proximal end of the shaft. In this manner, the balloon may be guided to the bifurcation on the first and second guide wires.

These and other objects and advantages of the present invention will be made apparent from the following detailed description, with reference to the accompanying drawings. In the drawings, the same reference numbers may be used to denote similar components in the various embodiments.

DETAILED DESCRIPTION OF THE INVENTION

The present invention is directed to a balloon catheter which is particularly useful in delivering and deploying a stent at or adjacent a bifurcation in a blood vessel. The invention may be used with any conventional balloon catheter delivery system, including an over-the-wire system or a rapid exchange system. In addition, the invention may be used to deploy any conventional balloon-deployable stent. Therefore, the scope of the present invention should not be limited to the particular embodiments discussed below.

Figure 1:
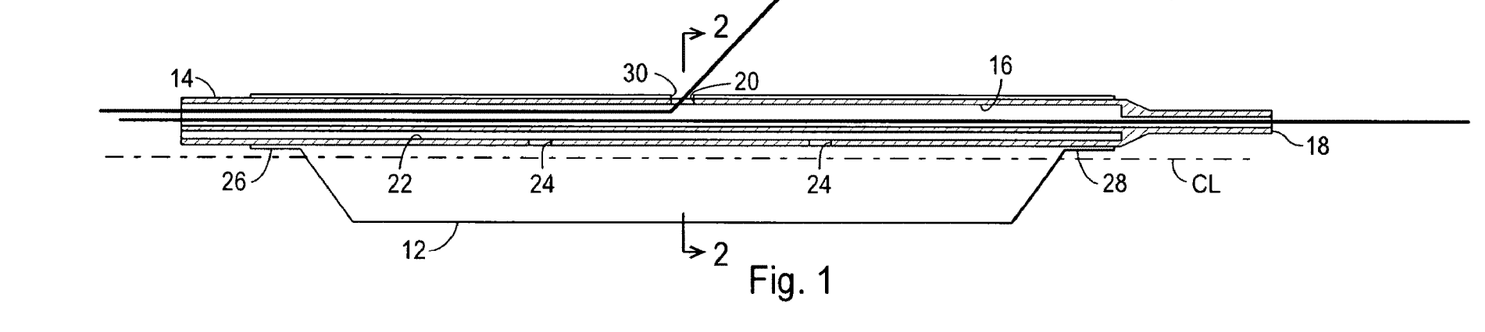
FIG. 1 is a longitudinal cross sectional view of one embodiment of the balloon catheter of the present invention shown in its inflated condition.
Figure 2:
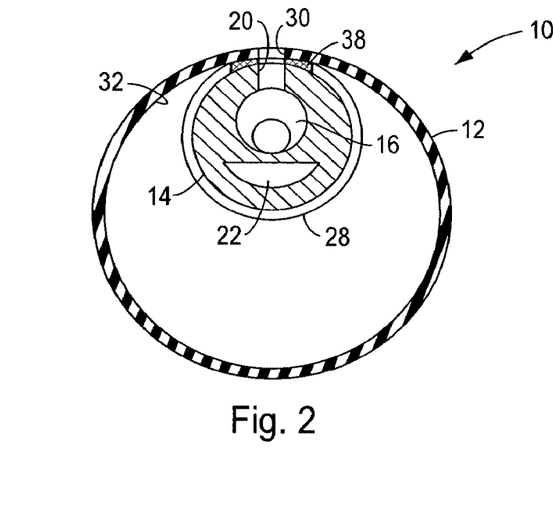
FIG. 2 is a cross sectional view of the balloon catheter of FIG. 1 taken along line 2-2.

Referring to FIGS. 1 and 2, the balloon catheter, generally 10, is shown to comprise a balloon 12 which is mounted on an elongated shaft 14, only the distal portion of which is shown. The shaft 14 comprises a proximal end, a distal end and a generally cylindrical side or outer surface. The shaft 14 also includes a guide wire lumen 16 which extends longitudinally through the shaft, a distal port 18 which extends from the guide wire lumen through the distal end of the shaft, a side port 20 which extends transversely from the guide wire lumen through the side surface of the shaft, an inflation lumen 22 which extends longitudinally through the shaft parallel to the guide wire lumen, and a number of inflation holes 24 which extend from the inflation lumen through the side of the shaft.

The balloon 12 comprises a first end 26 which is sealed to the shaft 14 proximally of the side port 20, a second end 28 which is sealed to the shaft distally of the side port and an aperture 30 which is aligned with the side port. The balloon 12 is inflated by pumping an inflation fluid through the inflation lumen 22 and the inflation ports 24 into the interior of the balloon. The balloon 12 is sealed to the shaft 14 proximate the side port 20 in a manner described below in order to prevent the inflation fluid from exiting the interior of the balloon through the aperture 30.

In accordance with the present invention, a longitudinal segment of the balloon 12 extending at least partially between the proximal and distal ends 26, 28 and encompassing the aperture 30 is bonded to the shaft 14 in order to maintain the side port 20 in close proximity to the exterior of the balloon during both its un-inflated and inflated conditions. As shown in FIGS. 1 and 2, for example, the aperture 30 is formed in the top segment of the balloon 12 and the inner surface 32 of the top segment is sealed to the shaft 14 along substantially the entire length of the balloon from the proximal end 26 to the distal end 28.

The proximal end 26, the distal end 28 and the longitudinal segment may be bonded to the shaft 14 by any conventional means, such as heat welding, ultrasonic welding or gluing. In one embodiment of the invention, for example, the proximal and distal ends 26, 28 and the longitudinal segment are glued to the shaft 14 using a conventional adhesive.

Figure 3:
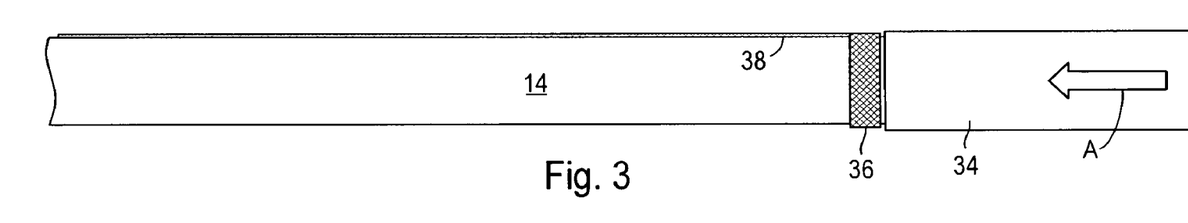
FIGS. 3-5 are representations illustrating the mounting of a balloon tube onto the shaft during the manufacture of the balloon catheter of the present invention.
Figure 4:
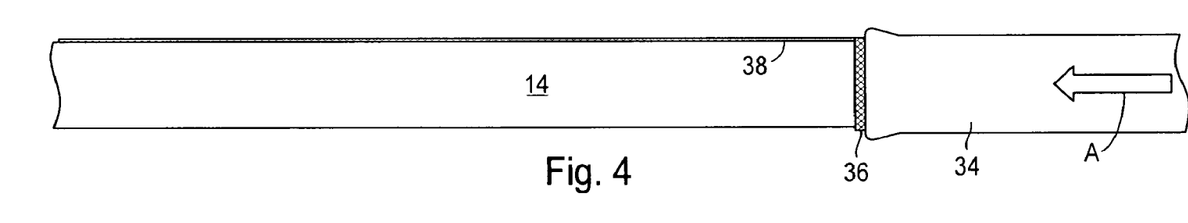
Figure 5:
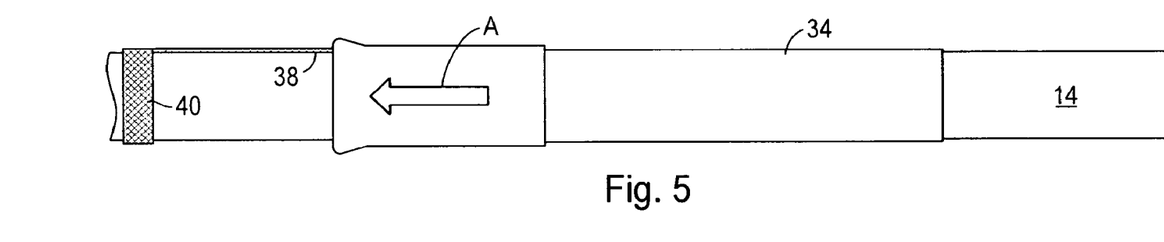

One method of accomplishing this is illustrated in FIGS. 3-5. First, a ring of adhesive 36 is applied around a portion of the shaft 14 to which the distal end 28 of the balloon 12 will be adhered, and a line of adhesive 38 is applied along a portion of the shaft to which the longitudinal segment of the balloon will be adhered. Then, a tube 34 made of an appropriate balloon material is positioned on the distal end of the shaft 14 and is advanced in the direction of the arrow A while the left edge (as viewed in FIG. 3) of the tube is held in place. As shown in FIG. 4, this will cause the balloon tube 34 to roll over onto itself and begin turning inside out. As the balloon tube 34 rolls over the ring of adhesive 36, the distal end 28 of the balloon 12 will be bonded to the shaft 14. As shown in FIG. 5, as the balloon tube 34 is further rolled out over the line of adhesive 38, the longitudinal segment of the balloon 12 will be bonded to the shaft 14. At an appropriate time, a second ring of adhesive 40 is applied around a portion of the shaft 14 to which the proximal end 26 of the balloon 12 will be adhered. The balloon tube 34 is then rolled over the second ring of adhesive 40 in order to bond the proximal end 26 of the balloon to the shaft.

In the un-inflated condition of the balloon 12, the portion of the balloon between the first and second ends 26, 28 comprises a longitudinal centerline CL which is coaxial with the axis of the shaft 14. As shown in FIG. 1, however, when the balloon 12 is inflated the longitudinal centerline CL is offset from the axis of the shaft 14. Since the first and second ends 26, 28 remain sealed to the shaft 14 at all times, the balloon takes on an eccentric configuration when inflated, that is, the longitudinal centerline CL of the portion of the balloon between the first and second ends 26, 28 is offset from the longitudinal centerline of the first and second ends. Although not required, the balloon tube 34 may be molded to have this eccentric configuration either before or after mounting on the shaft 14.

Due to the fact that the balloon 12 comprises an eccentric configuration when inflated, and because the shaft 14 is adhered to a segment of the balloon which is aligned with the first and second ends 26, 28, the balloon will expand to its full diameter over substantially its entire length between the first and second ends. Consequently, when the balloon catheter 10 is used to deploy a stent, the stent will also be fully expanded over its entire length.

After the balloon 12 is mounted on the shaft 14, a suitable tool may be used to form the aperture 30 and the side port 20 through the balloon 12 and the shaft 14 in a single step. As shown in FIG. 2, the aperture 30 and the side port 20 are ideally formed through the line of adhesive 38 to ensure that the aperture is sealed to the shaft 14 in order to prevent the inflation fluid from leaking out of the balloon 12.

Figure 6:
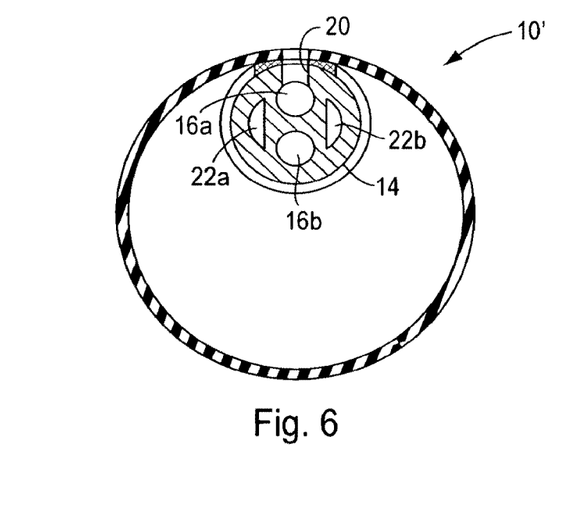
FIG. 6 is a cross sectional view of a second embodiment of the balloon catheter of the present invention.

Another embodiment of the invention is shown in FIG. 6. The balloon catheter of this embodiment, generally 10', is similar in most respects to the balloon catheter 10 described above. In this embodiment, however, the shaft 14 comprises two separate guide wire lumens 16a, 16b, one of which is connected to the distal port 18 and the other of which is connected to the side port 20. The shaft 14 may also include two inflation lumens 22a, 22b, each of which is connected to the interior of the balloon 12 through respective inflation holes.

The procedure for stenting a bifurcation using the balloon catheter of the present invention is illustrated in FIGS. 7-16. First, a first coronary guide wire 42 is inserted into the main vessel M and a second coronary guide wire 44 is inserted into the side branch vessel S. These guide wires remain in position during the entire procedure in order to preserve access to both vessels at all times. A conventional preliminary balloon angioplasty may then be performed to pre-dilate the lesions.

Figure 7:
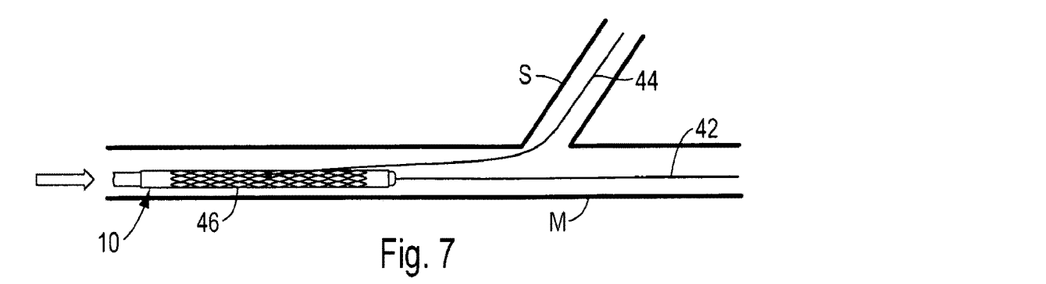
FIGS. 7 through 16 are representations of the balloon catheter of FIG. 1 being used to treat bifurcation lesions (the lesions having been omitted for purposes of clarity).
Figure 8:
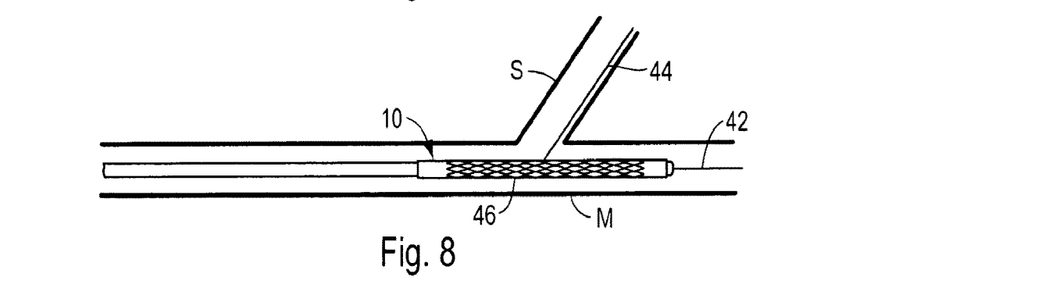
Figure 9:
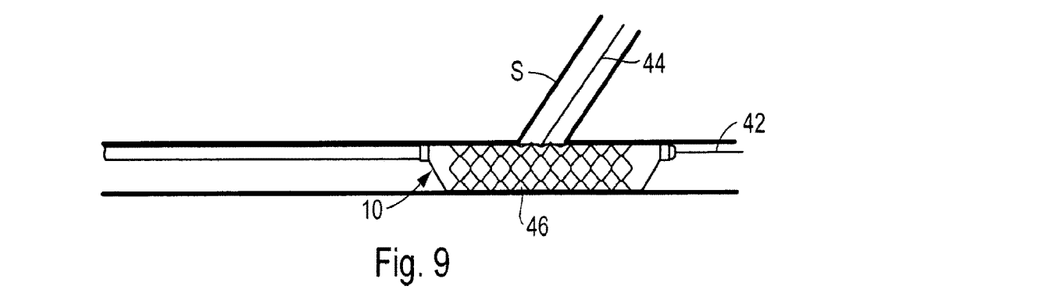
Figure 10:
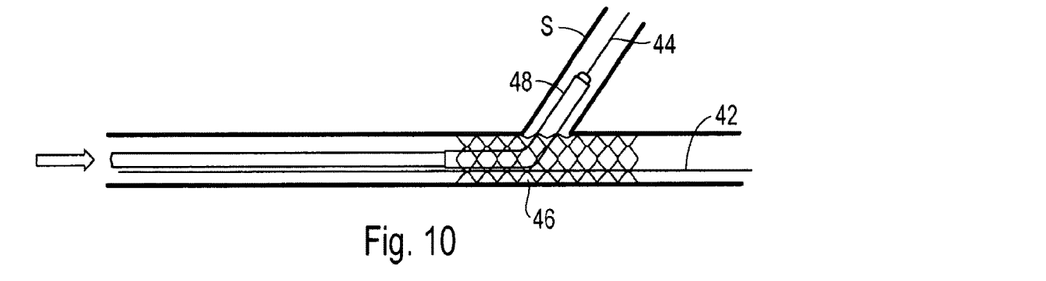

In order to stent the main vessel, a balloon catheter 10 with a conventional stent 46 mounted thereon is loaded onto the guide wires by back feeding the main guide wire 42 into the distal port 18 and back feeding the side-branch guide wire 44 through the stent and into the side port 20. The balloon catheter 10 is then guided along the guide wires to the bifurcation (FIG. 7). Due to the relationship between the side branch S, the side-branch guide wire 44 and the side port 20, the side port is automatically positioned opposite and oriented toward the side branch (FIG. 8). The balloon 12 is then inflated to install the stent in the main vessel M (FIG. 9). The balloon catheter 10 is then withdrawn and removed from the guide wires, after which a conventional balloon catheter 48 may be loaded onto the side-branch guide wire 44, guided through the main stent 46 and then expanded in order to open the struts covering the side branch S, if necessary (FIG. 10).

Figure 11:
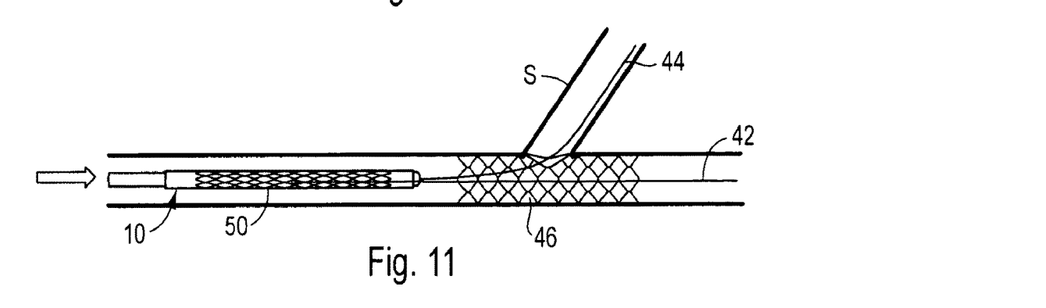
Figure 12:
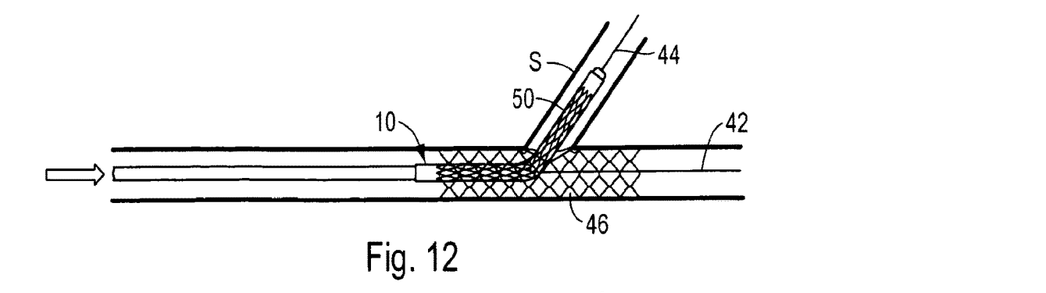
Figure 13:
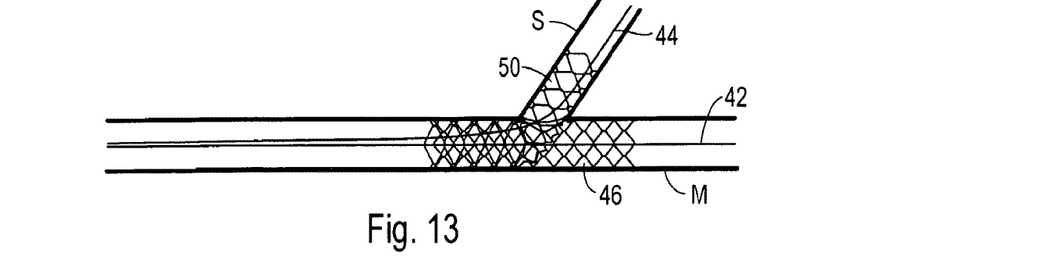

In order to then stent the side branch vessel S, a second balloon catheter 10 with a second conventional stent 50 mounted thereon is loaded onto the guide wires by back feeding the side-branch guide wire 44 into the distal port 18 and back feeding the main guide wire 42 through the stent and into the side port 20. The balloon catheter 10 is then advanced along the guide wires toward the bifurcation (FIG. 11). If the culotte technique is to be employed, the balloon catheter 10 is advanced until approximately the distal half of the balloon 12 passes through the main stent 46 and is positioned in the side branch vessel S (FIG. 12). The balloon 12 is then inflated to deploy the stent 50 in both the main vessel M and the side branch vessel S (FIG. 13).

Figure 14:
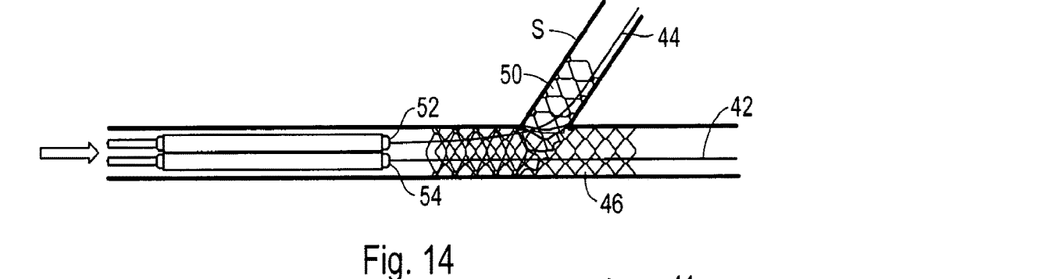
Figure 15:
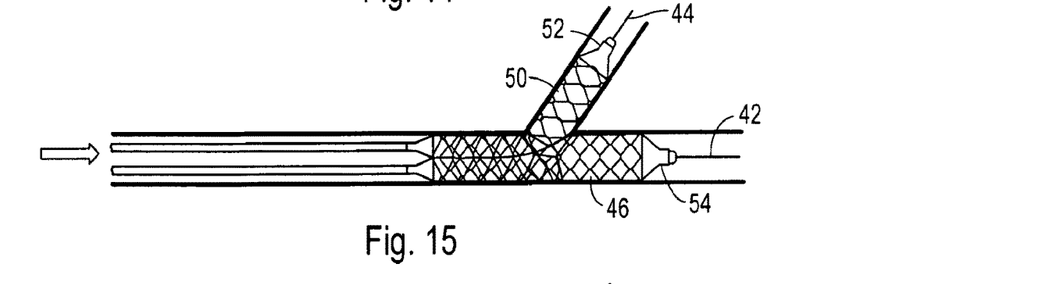
Figure 16:
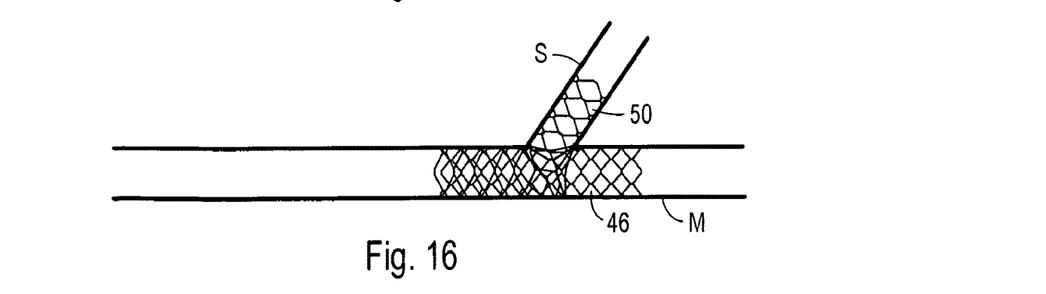

After the balloon catheter 10 is withdrawn, the kissing balloon technique may be employed in order to fully expand the stents. To do this, one balloon 52 is loaded onto the main guide wire 42, a second balloon 54 is loaded onto the side-branch guide wire 44, and the balloons are advanced together toward the bifurcation until the distal portion of the side-branch balloon is positioned in the side branch vessel (FIG. 14). The balloons are then inflated simultaneously in order to fully expand both stents (FIG. 15). The resulting coverage is similar to what is obtained using the conventional culotte technique (FIG. 16).

The segmented balloon catheter of the present invention can also be used with other stenting techniques. For example, the T-stenting technique can be performed very easily by following the above-described procedure.

Figure 17:
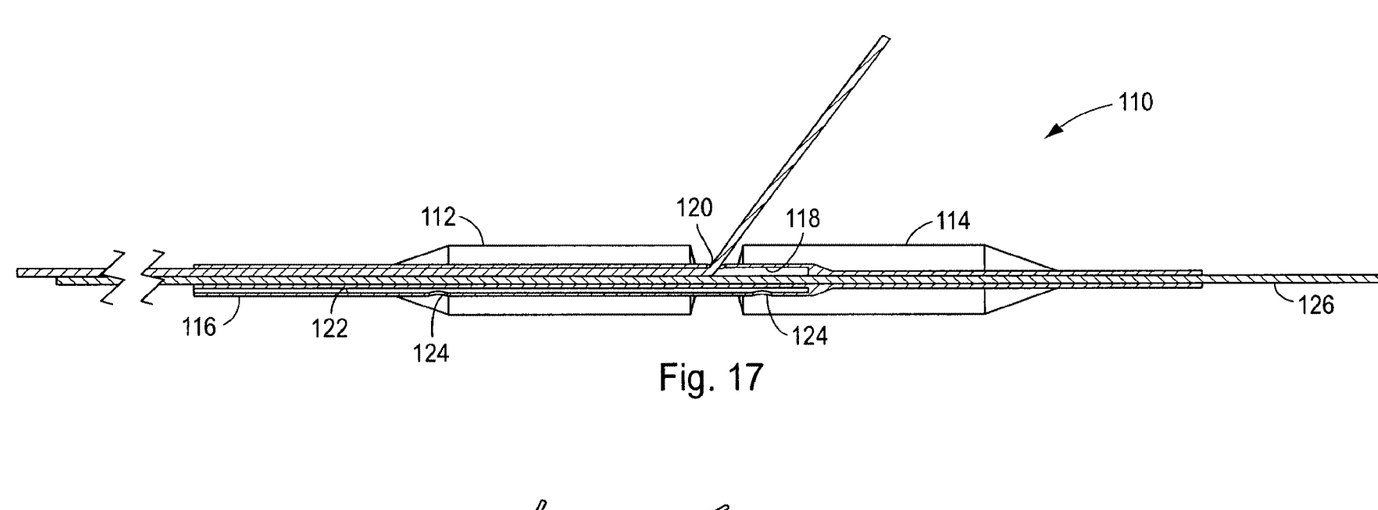
FIG. 17 is a longitudinal cross sectional view of a third embodiment of the balloon catheter of the present invention shown in its inflated condition.
Figure 18:
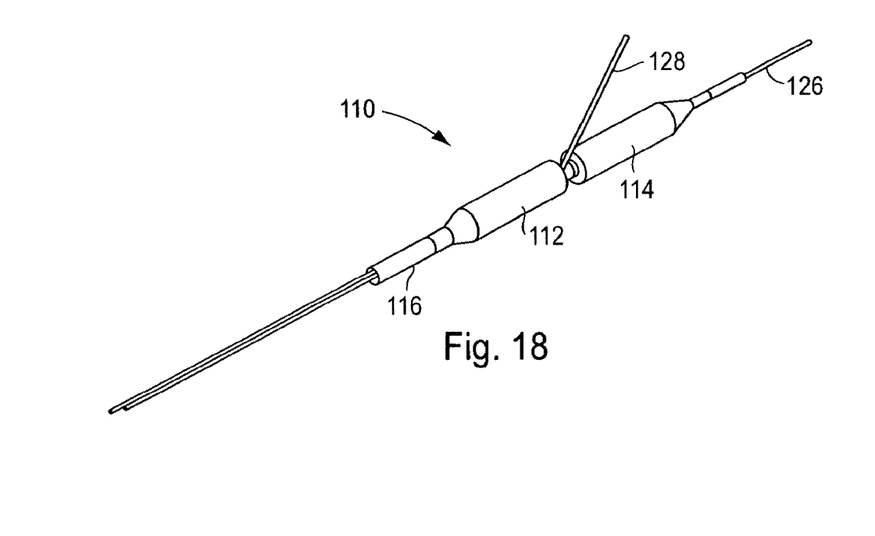
FIG. 18 is a perspective view of the balloon catheter shown in FIG. 17.
Figure 19:
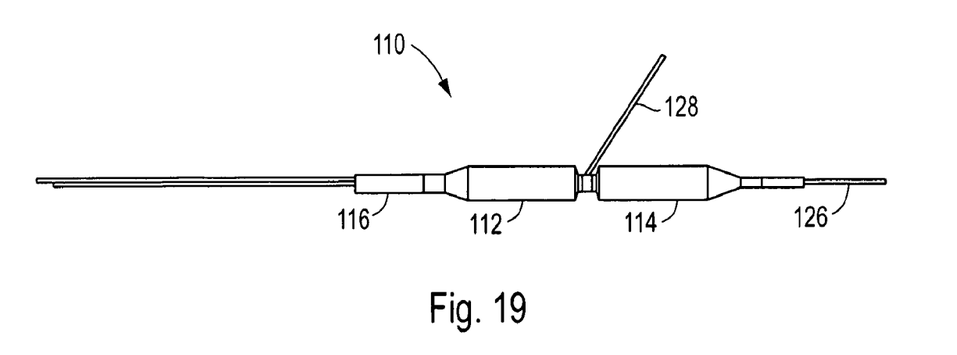
FIG. 19 is a side elevation view of the balloon catheter shown in FIG. 17.

Another embodiment of the balloon catheter of present invention will be described with reference to FIGS. 17 through 19. The balloon catheter of this embodiment, generally 110, is similar in many respects to the balloon catheter described in U.S. Pat. No. 6,761,734, which is hereby incorporated herein by reference. Thus, the balloon catheter 110 includes first and second balloons 112, 114 which are mounted side by side on a common shaft 116. The shaft 116 comprises a single guide wire lumen 118 which can be accessed through both the distal end of the shaft and through a side port 120 located between the two balloons. The shaft 116 also includes a separate inflation lumen 122 which is connected to the interior of the balloons 112, 114 through corresponding inflation ports 124.

In use, a conventional stent (not shown) is mounted on the balloons 112, 114 over the side port 120. First and second guide wires 126, 128, which preferably have already been pre-inserted in the vessels to be treated, are then back fed into guide wire lumen 118 through the distal end of the shaft 116 and through the side port 120, respectively.

The procedure for treating bifurcation lesions with the segmented balloon catheter 110 is similar to that discussed above in connection with FIGS. 7-16. In addition, this segmented balloon catheter can also be used with other stenting techniques, such as the T-stenting technique.

Figure 20:
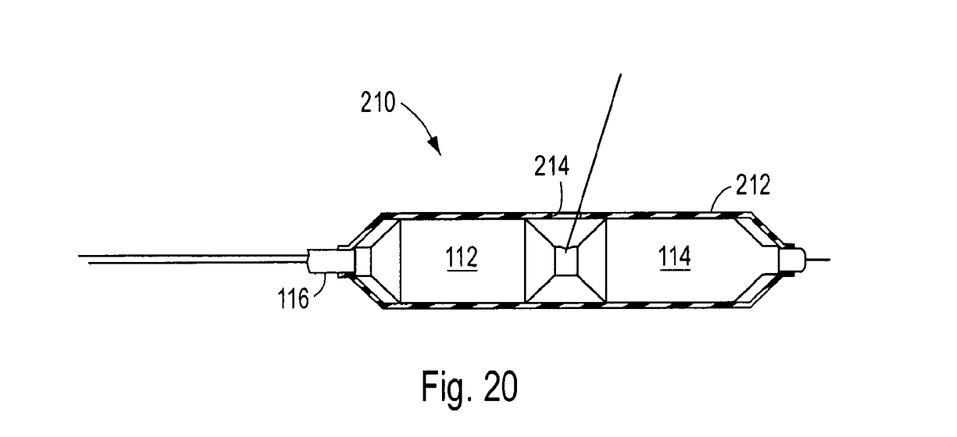
FIG. 20 is a longitudinal cross sectional view of a fourth embodiment of the balloon catheter of the present invention shown in its expanded condition.
Figure 21:
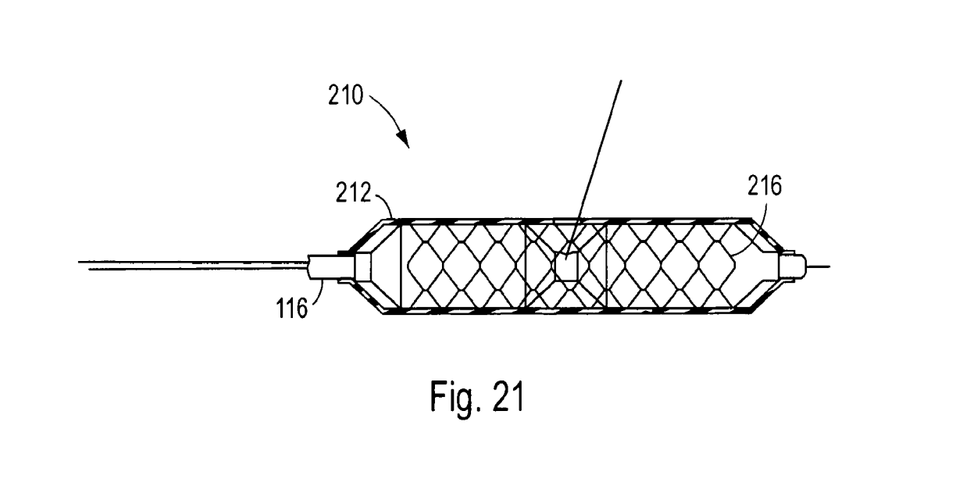
FIG. 21 is a longitudinal cross sectional view of the balloon catheter of FIG. 17 shown with an exemplary stent mounted thereon.

Another embodiment of the balloon catheter of the present invention is shown in FIGS. 20 and 21. The balloon catheter of this embodiment, generally 210, is similar in many respects to the balloon catheter 110 described above. In this embodiment, however, a third balloon 212 is mounted on the shaft 116 over both the first and second balloons 112, 114. The third balloon 212 is not connected to the inflation lumen 122. Instead, the third balloon 212 is expanded when the first and second balloons 112, 114 are inflated. The third balloon 212 also includes a side port 214 which, when the balloons are in their un-inflated condition, aligns with the side port 120 in the shaft 116 to allow a guide wire to be back fed through the third balloon and into the side port.

In use of the balloon catheter 210, a conventional stent 216 is mounted over the third balloon. When the first and second balloons 112, 114 are inflated, they will force the third balloon 212 to expand to the diameter of the first and second balloons, even in the intermediate area between the balloons. As a result, the stent 216 will expand completely over its entire length.

The procedure for treating bifurcation lesions with the segmented balloon catheter 210 is similar to that discussed above in connection with FIGS. 7-16. Moreover, this segmented balloon catheter can also be used with other stenting techniques, such as the T-stenting technique.

Figure 22:
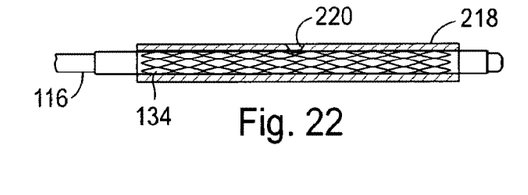
FIG. 22 is a longitudinal cross sectional view of a fifth embodiment of the balloon catheter of the present invention shown in its unexpanded condition.
Figure 23:
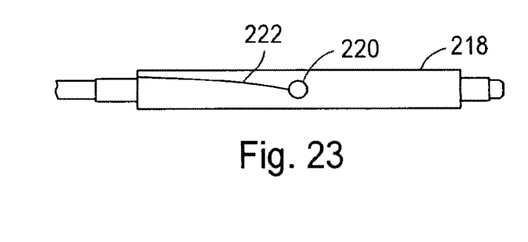
FIG. 23 is a side elevation view of the balloon catheter shown in FIG. 22.

Referring now to FIGS. 22 and 23, a guide sleeve 218 is disclosed which can be used with any of the balloon catheter embodiments described above to facilitate back feeding the guide wire into the side port, such as the side port 120 of the balloon catheter 110. The guide sleeve 218, which is mounted over the stent after the stent is mounted over the balloons 112, 114, includes a guide port 220 which aligns with the side port 120 in the shaft 116. The guide port 220 provides a larger opening than the side port 120 into which the guide wire can be inserted. In this regard, the guide port 218 may have an enlarged, generally circular outer opening which tapers to approximately the diameter of the side port 120.

The guide sleeve 218 preferably also includes a slit 222 which extends from the guide port 220 to the ends of the sleeve. This will allow the guide sleeve 218 to be removed from the balloon catheter 110 once the guide wire has been back fed into the side port 120.

It should be recognized that, while the present invention has been described in relation to the preferred embodiments thereof, those skilled in the art may develop a wide variation of structural and operational details without departing from the principles of the invention. Therefore, the appended claims are to be construed to cover all equivalents falling within the true scope and spirit of the invention.

I claim:

1. A balloon catheter for use in treating a condition of a vessel occurring near a bifurcation defined by the intersection of a main vessel with a side branch vessel, the balloon catheter comprising:
    a shaft which includes a proximal end, a distal end and a side surface;
    a single guide wire lumen which extends longitudinally through the shaft;
    a distal port which extends from the guide wire lumen through the distal end of the shaft;
    a side port which extends transversely from the guide wire lumen through the side surface of the shaft; and
    a balloon which is formed separately from the shaft, the balloon being mounted on the shaft and comprising a first end which is sealed to the shaft proximally of the side port, a second end which is sealed to the shaft distally of the side port, an aperture which is aligned with the side port, and a longitudinal segment which extends from the first end to the second end and is entirely sealed to the shaft, said aperture being located in said longitudinal segment such that a portion of the balloon surrounding the aperture is sealed to the shaft around the side port;
    wherein the balloon is configured such that, in an inflated condition the balloon comprises a longitudinal centerline which is radially offset from a longitudinal centerline of the shaft;
    wherein in use of the balloon catheter a proximal end of a first guide wire which is pre-positioned in the main vessel is inserted into the distal port and threaded through the guide wire lumen toward the proximal end of the shaft and a proximal end of a second guide wire which is pre-positioned in the side branch vessel is inserted into the side port and threaded through the guide wire lumen toward the proximal end of the shaft;
    whereby the balloon is guided to the bifurcation on the first and second guide wires;
    a stent which is mounted on the balloon; and
    means for guiding the proximal end of the second guide wire into the side port.

2. The balloon catheter of claim 1, wherein the guiding means comprises a cylindrical guide sleeve which is mounted over the stent and which includes a guide port that is aligned with the side port.

3. The balloon catheter of claim 2, wherein the guide port comprises an inner opening which is located on an inner surface of the sleeve and an outer opening which is located on an outer surface of the sleeve in alignment with the inner opening, and wherein the inner opening comprises a diameter approximately the same as a diameter of the side port and the outer opening comprises a diameter larger than the diameter of the inner opening.

4. The balloon catheter of claim 2, wherein the guide sleeve comprises at least one slit which extends longitudinally from the guide port to an axial end of the sleeve.

5. A balloon catheter for use in treating a condition of a vessel occurring near a bifurcation defined by the intersection of a main vessel with a side branch vessel, the balloon catheter comprising:
- a shaft which includes a single guide wire lumen, a distal port which extends from the guide wire lumen through a distal end of the shaft, and a side port which extends from the guide wire lumen through a side of the shaft;
- a balloon which is formed separately from the shaft, the balloon being mounted on the shaft and including a first end which is sealed to the shaft proximally of the side port, a second end which is sealed to the shaft distally of the side port, a longitudinal segment which extends from the first end to the second end over the side port, and an aperture which is formed in the longitudinal segment and is aligned with the side port;
- wherein the entire longitudinal segment is sealed to the shaft such that a portion of the balloon surrounding the aperture is sealed to the shaft around the side port;
- wherein when the balloon is in an inflated condition, the balloon comprises a longitudinal centerline which is radially offset from the shaft;
- a stent which is mounted on the balloon; and
- means for guiding an end of a guide wire lumen into the side port.

6. The balloon catheter of claim 5, wherein the guiding means comprises a cylindrical guide sleeve which is mounted over the stent and which includes a guide port that is aligned with the side port.

7. The balloon catheter of claim 6, wherein the guide port comprises an inner opening which is located on an inner surface of the sleeve and an outer opening which is located on an outer surface of the sleeve in alignment with the inner opening, and wherein the inner opening comprises a diameter approximately the same as a diameter of the side port and the outer opening comprises a diameter larger than the diameter of the inner opening.

8. The balloon catheter of claim 6, wherein the guide sleeve comprises at least one slit which extends longitudinally from the guide port to an axial end of the sleeve.

\* \* \* \* \*